United States Patent [19]

Neumann et al.

[11] Patent Number: 4,791,227

[45] Date of Patent: Dec. 13, 1988

[54] METHOD FOR HANDLING REACTION MIXTURES CONTAINING HYDROGEN FLUORIDE

[75] Inventors: Alfred Neumann, Raunheim; Willi Ploesser, Seeheim-Jugenheim; Hermann-Josef Siegert, Darmstadt, all of Fed. Rep. of Germany

[73] Assignee: Röhm GmbH, Darmstadt, Fed. Rep. of Germany

[21] Appl. No.: 422,254

[22] Filed: Sep. 23, 1982

[30] Foreign Application Priority Data

Oct. 6, 1981 [DE] Fed. Rep. of Germany ....... 3139653

[51] Int. Cl.⁴ .................. C07C 67/38; C07C 67/54; C07C 67/58; C07C 51/14; C07C 51/44; C07C 51/48
[52] U.S. Cl. .................. 562/521; 203/86; 203/DIG. 6; 203/DIG. 16; 260/413; 260/419; 260/410.9 R; 423/415 A; 562/606; 560/233
[58] Field of Search .................. 562/521, 606; 423/415 A; 260/413, 419, 410.9 R; 203/86, DIG. 6, DIG. 16; 560/233

[56] References Cited

U.S. PATENT DOCUMENTS

| | | | |
|---|---|---|---|
| 3,910,963 | 10/1975 | Souma et al. | 260/343 |
| 4,039,564 | 8/1977 | Schmerling et al. | 562/521 |
| 4,452,999 | 6/1984 | Besccke et al. | 560/233 |

FOREIGN PATENT DOCUMENTS 582745 9/1959 Canada .................. 562/521
31886 7/1981 European Pat. Off. .

OTHER PUBLICATIONS

Perry et al., Chemical Engineers Handbook, 5th ed., McGraw-Hill Book Co., N.Y., 1973, pp. 23–44.
Dechema Materials Table, No. DWT 699, Nov. 1957.
"Corrosion Resistance of Ni–Containing Alloys, Etc.", Int'l. Nickel Ltd., London, Mar. 1979.
Publication 36823G, Henry Wiggin Co., Hereford, England, Mar. 1977.
Takezaki et al., Bull. Japan Petroleum Inst. 8, 31–38 (1966).
Rabald et al., Dechema Werkstoff Tabelle DWT 699, Nov. 1957.

Primary Examiner—Vivian Garner
Attorney, Agent, or Firm—Curtis, Morris & Safford

[57] ABSTRACT

What is disclosed is the use of metallic vessels having particularly high corrosion resistance which are made of (a) aluminum or alloys containing more than 95% aluminum, or of (b) nickel-chromium-iron alloys containing from 30 to 50% of nickel, from 20 to 30% of chromium, and from 18 to 50% of iron, by weight, in reacting or working up mixtures containing substantial amounts of hydrogen fluoride in addition to organic carboxylic acids and/or carbon monoxide and/or water.

7 Claims, No Drawings

METHOD FOR HANDLING REACTION MIXTURES CONTAINING HYDROGEN FLUORIDE

The present invention relates to methods for the reacting or working up of mixtures which contain substantial amounts of hydrogen fluoride using vessels of particular metals.

More in particular the mixtures may, in addition to hydrogen fluoride, contain organic carboxylic acids and/or water and/or carbon monoxide. Mixtures of this kind are produced in the Koch carboxylic acid synthesis when hydrogen fluoride is used as a Koch catalyst.

It goes without saying that working with hydrogen fluoride requires the use of construction materials which are resistant to it. This is true even of laboratory scale batches, for which glass vessels are not suited. U.S. Pat. No. 3,910,963 mentions equipment made of polymers of fluorochlorohydrocarbons. Takezaki et al. [Bulletin of the Japan Petroleum Institute, 8, 3–38, particularly page 32, (1966)] report the use of a stainless-steel autoclave in systematic tests.

In small-scale experiments, these construction materials are not severely damaged by hydrogen fluoride or by mixtures which, in addition to hydrogen fluoride, contain other corrosive components. However, in industrial-scale operation, and particularly in continuous operation, considerably higher resistance is required.

According to E. Rabald and H. Bretschneider (DE-CHEMA List of Materials of Construction DWT 699, November 1957), for industrial purposes silver and nickel, as well as nickel alloys and particularly Monel metal, an alloy of nickel and copper, are regarded as the materials possessing the highest resistance to corrosion by hydrogen fluoride under a wide variety of conditions. In European patent application 31 886, too, equipment made of nickel or nickel alloys is recommended for carrying out the synthesis on an industrial scale of isobutyric acid from propylene, carbon monoxide and water in the presence of hydrogen fluoride as a Koch catalyst. Cited as examples are the nickel alloys known under the tradenames "Monel", "Inconel", and "Hastelloy", and in particular an alloy of 64% Ni, 16% Cr, 3% Fe, 16% Mo, 1% Mn and 2% Co ("Hastelloy C4").

In practice, unexpected problems have been encountered in the use of these metals. While the last-mentioned alloy has proved corrosion resistant under the conditions of the Koch carboxylic acid synthesis, it is so expensive (presumably because of its high molybdenum content) that the fabrication of an industrial high-pressure reactor from the metal results in intolerably high equipment costs.

Contrary to the expectations which one skilled in the art might have in the light of the tables on industrial construction materials, it has been found that nickel itself and many of its alloys, and particularly Monel metal, which is regarded as HF-resistant, cannot withstand the highly corrosive mixtures of the Koch carboxylic acid synthesis at temperatures above 80° C. or 100° C. It has been observed that as much as several millimeters of material may be removed per year. Thus, what is known about resistance to corrosion by hydrogen fluoride or hydrofluoric acid is not applicable to the mixtures of the Koch synthesis, which may, in addition, contain organic carboxylic acids and carbon monoxide. There has therefore been a need to find a metal which can satisfy the requirements to be met and which, because of its low content of high-grade alloying elements, is available at a price that makes it possible to fabricate affordable equipment for the reaction and working-up of such corrosive mixtures.

According to the present invention, such equipment for reacting and treating reaction mixtures containing HF, and particularly reaction mixtures from the Koch synthesis containing still other corrosive components, can be made from aluminum, aluminum alloys containing more than 95 percent by weight of aluminum, or from nickel-chromium-iron alloys containing 30 to 50 percent by weight of nickel, 20 to 30 percent by weight of chromium, and 18 to 50 percent by weight of iron.

Aluminum has less corrosion resistance than the nickel-chromium-iron alloys mentioned above. However, because of its low price, it can be used to advantage where some consumption of the construction material can be tolerated, or when the vessel is not expected to have a long service life, or when the consumption of the construction material proceeds at a slower rate because of lower temperatures, for example, or because of lower corrosiveness.

Suitable for use are pure aluminum or aluminum alloys with at least 95% by weight, and preferably at least 99% by weight, of Al with small amounts of other elements such as Cu, Mg, and Si.

Nickel-chromium-iron alloys are preferred. They contain from 30 to 50 weight percent of Ni, from 20 to 30 weight percent of Cr, and from 18 to 50 weight percent of Fe. They may further contain minor amounts of other metals, for example Mo, Mn, Co, W, Cu, and Nb. The total amount of these last-mentioned metals should be under 20 weight percent and the amount of each last-mentioned individual metal should be under 10 weight percent.

Preferred alloys of this group are composed of 30 to 45 weight percent of Ni, 20 to 25 weight percent of Cr, and 30 to 50 weight percent of Fe. Since these alloys are lower in Ni and Cr, though higher in Fe, they are particularly low in cost. Yet their corrosion resistance is not lower than that of alloys having a higher Ni and Cr content. Best with regard to cost and corrosion behavior are alloys of the composition 30 to 40 weight percent of Ni, 20 to 25 weight percent of Cr, and 40 to 50 weight percent of Fe. As a rule, these alloys do not contain further alloying elements.

The increased corrosion resistance of the metals defined can be demonstrated by a corrosion treatment for 500 hours under the conditions of the Koch synthesis. Test specimens of the metals under investigation were exposed to a Koch synthesis reaction mixture containing about 70 weight percent of hydrogen fluoride, 30 weight percent of isobutyric acid, and minor amounts of other constituents at 120° C. under a CO pressure of 120 bars in such a way that one test specimen was located in the liquid phase and the other in the gas phase. After 500 hours' exposure, a readily removable encrustation was scraped off with a brass brush and the weight loss determined and converted to reduction in thickness per year.

|  | Alloy (Weight percent) | | | | Metal consumption in liquid phase (mm/yr) |
|---|---|---|---|---|---|
|  | Ni | Fe | Cr | Others |  |
| (A) | 46 | 19.5 | 22 | 6.5 Mo, 1.5 Mn, 2.5 Co, 1 W | 0.11 |
| (B) | 46.5 | 19.5 | 22 | 7 Mo, 5 Co, 1.5 W, 1.9 Cu | 0.09 |
| (C) | 40 | 33.3 | 21 | 3 Mo, 2 Cu | 0.06–0.003 |
| (D) | 32 | 46.3 | 21 |  | −0.084* |
| (E) |  | 0.2 |  | Aluminum (99.5%), 0.2 Si | 0.9 |
| Comparison with other HF-resistant alloys: | | | | | |
| (F) | Pure nickel | | | | 9.8 |
| (G) | Monel metal (65% Ni, 34% Cu, 1% Mn) | | | | 25 |

*Alloy (D) showed a weight gain (mathematically a negative consumption value) and developed a solid, smooth, enamel-like coating that could not be scraped off with a brass brush.

The consumption of metal in the gas phase generally was even lower than in the liquid phase, but in the case of pure nickel was higher, namely 11.3 mm/yr.

The metals designated (A) to (E) are considerably cheaper than alloys which because of a high molybdenum content, are designed for extreme corrosion resistance. In the alloys used in accordance with the invention, the molybdenum content is always less than 10 weight percent.

The corrosive action of mixtures containing substantial amounts of hydrogen fluoride in addition to organic carboxylic acids, water, and/or carbon monoxide is encountered both in the reacting of such mixtures (and particularly in the Koch synthesis) and in the working up of the reaction mixture, for example by distillation or extraction. Reaction equipment includes not only reactors but also pipelines, valves, pumps, and other apparatus through which the mixture is fed to the reactor or withdrawn from it. Working-up equipment includes, for example, heat exchangers, distillation and extraction columns, storage and intermediate tanks, and the auxiliary equipment mentioned in connection with the reaction equipment. All these equipment components are referred to in the present specification and claims as "vessels" to the extent that they are adapted to contain the corrosive mixture in their interior.

In accordance with the invention, the vessels intended to come into contact with the corrosive mixture are fabricated from the metals defined, or are lined therewith, and are used in reacting and working up the mixtures.

From the point of view of manufacture, vessels made entirely of these metals are preferred. However, with respect to corrosion resistance it will suffice if at least the layer of the metal wall which faces the interior of the vessel is made of the metals defined. The minimum thickness of that layer will depend on the amount of metal consumed over the expected service life. For example, if the metal consumption is likely to range from 0.01 to 0.1 mm/yr. and the equipment is to be kept in service for at least 10 years, the thickness of the layer should range at least from 0.1 to 1 mm. Layers ranging in thickness from 0.5 to 5 mm are preferred when corrosion damage is to be positively prevented. Such a layer structure is especially indicated for pressure vessels capable of withstanding pressures of 100 bars and up, for example. The outer layer may form by far the major portion of the wall and be formed of a steel that is not corrosion resistant. Occasionally, reactors are provided with a nonmetallic and usually ceramic inner liner. Such liners are not impervious to corrosive contents in the vessels. For this reason, the side of the metal wall facing the interior should be structured in accordance with the invention also in these cases.

Corrosion conditions may very widely at different points in an industrial scale installation. For reasons of cost, it is therefore advisable to use cheaper construction materials having correspondingly lower corrosion resistance at points less susceptible to attack. In some cases it will suffice to use vessels made of the metals defined only where temperatures ranging from 80° to 160° C., and more particularly from 100° to 140° C., are employed or encountered.

The composition of the mixtures may also vary at different points and may require different corrosion resistances. Mixtures containing "substantial amounts of hydrogen fluoride" are mixtures containing at least 30 weight percent of HF. The term "mixture" as used in the specification and claims means not only homogeneous liquid or gaseous phases, but also separate liquid or gaseous phases of the same chemical composition or of different compositions that may be present concurrently in a vessel.

The mixtures used in a reaction often contain no carboxylic acid but sometimes contain water which, when present in a proportion exceeding 5 percent, based on the total weight of the contents of the vessel, will produce an appreciable increase in corrosiveness. Organic carboxylic acids in concentrations of over 10 weight percent also have a corrosion-stimulating effect.

It is believed that carbon monoxide has a corrosive effect on nickel containing alloys due to the formation of carbonyls. It has a particularly corrosive effect at CO partial pressures above 10 bars. While this may explain the inadequate resistance of nickel and Monel metal, it does not explain the surprising corrosion resistance of iron containing alloys since iron itself forms carbonyls. The highest corrosive stresses usually act on the reactor itself since that is where all starting and end products are present at the same time and where the temperatures and pressures are usually high. The vessels used in accordance with the invention thus are preferably used as reactors.

The use of the vessels in continuously operated reaction and working-up installations is a preferred field of application of the invention. The Koch synthesis using a reaction mixture containing substantial amounts of propylene, carbon monoxide, hydrogen fluoride, and possibly water or a lower alkanol is the major field of use.

What is claimed is:

1. A method for reacting, distilling, or extracting a Koch reaction mixture comprising propylene, carbon monoxide, and a substantial amount of hydrogen fluoride at a temperature betwween 80° C. and 160° C. and under pressure conditions usually employed in the Koch synthesis in a metal vessel having an interior wall wherein at least said interior wall of said vessel is made of
    (a) aluminum, or of an aluminum alloy containing more than 95 percent by weight of aluminum, or of
    (b) a nickel-chromium-iron alloy containing from 30 to 50 percent by weight of nickel, from 20 to 30 percent by weight of chromium, and from 18 to 50 percent by weight of iron.

2. A method as in claim 1 wherein said reacting involves a continuous reaction method.

3. A method as in claim 1 wherein said mixture additionally contains water or a lower alcohol.

4. A method as in claim 1 wherein at least said interior wall of said vessel is made of an alloy containing from 20 to 25 percent by weight of chromium, from 30 to 45 percent by weight of nickel, and from 30 to 50 percent by weight of iron.

5. A method as in claim 1 wherein at least said interior wall of said vessel is made of an alloy containing from 20 to 25 percent by weight of chromium, from 30 to 40 percent by weight of nickel, and from 40 to 50 percent by weight of iron.

6. A method as in claim 1 wherein said metal vessel is a pressure vessel capable of withstanding a pressure of at least 100 bars.

7. A method as in claim 1 wherein said temperature is between 100° C. and 140° C.

* * * * *